(12) United States Patent
Howard

(10) Patent No.: US 6,806,088 B2
(45) Date of Patent: Oct. 19, 2004

(54) METHOD AND APPARATUS FOR IMPROVING THE PERFORMANCE OF MICROANALYTIC AND MICROSYNTHETIC PROCEDURES

(75) Inventor: John K. Howard, Saratoga, CA (US)

(73) Assignee: Matsushita Electric Industrial Co., Ltd., Osaka (JP)

(*) Notice: Subject to any disclaimer, the term of this patent is extended or adjusted under 35 U.S.C. 154(b) by 430 days.

(21) Appl. No.: 09/827,895

(22) Filed: Apr. 9, 2001

(65) Prior Publication Data

US 2002/0146699 A1 Oct. 10, 2002

(51) Int. Cl.$^7$ ............................................... G01N 31/20
(52) U.S. Cl. ........................... 436/45; 422/64; 422/67; 422/72; 436/50
(58) Field of Search ............................. 422/64, 67, 72; 436/45, 50

(56) References Cited

U.S. PATENT DOCUMENTS

| | | | |
|---|---|---|---|
| 4,868,819 A | * 9/1989 | Kimura | .................... 369/30.13 |
| 6,030,581 A | 2/2000 | Virtanen | |
| 6,063,589 A | 5/2000 | Kellogg et al. | |
| 6,121,048 A | * 9/2000 | Zaffaroni et al. | .............. 436/45 |
| 6,256,738 B1 | * 7/2001 | Sinquin et al. | ............. 713/194 |
| 6,319,469 B1 | * 11/2001 | Mian et al. | .................... 422/64 |
| 6,724,706 B1 | * 4/2004 | Nakajima et al. | ........ 369/59.23 |

OTHER PUBLICATIONS

Http://www.padus.com/support/manuals/401/html/08_Advanced_Concepts/01_Capacity (Jun. 14, 2004).*

* cited by examiner

*Primary Examiner*—Jan M. Ludlow
(74) *Attorney, Agent, or Firm*—McDermott Will & Emery LLP

(57) ABSTRACT

In a first exemplary embodiment, the present invention relates to an apparatus for performing an assay comprising a micro-system platform, a CD-ROM device and an information processor, where the CD-ROM device under control of the information processor is capable of reading and writing data to the micro-system platform. The micro-system platform comprises a first section for storing data in a continuous circular data band, which is disposed in an inner portion of the micro-system platform, and a second section including at least one assay, which is formed in an outer portion of the micro-system platform. During operation, the CD-ROM device retrieves and stores data related to the performance of the assay in the circular data band. The information processor is operative for controlling the CD-ROM device in accordance with the data retrieved from the circular data band, and for analyzing the results of the assay.

35 Claims, 2 Drawing Sheets

METHOD AND APPARATUS FOR IMPROVING THE PERFORMANCE OF MICROANALYTIC AND MICROSYNTHETIC PROCEDURES

FIELD OF THE INVENTION

This invention relates generally to diagnostic assays, and more particularly, to a method and apparatus for configuring both data and assays (e.g., micro-system platforms) on a single compact disk.

BACKGROUND OF THE INVENTION

Prior to the present invention, it has been known to provide clinical assays/micro-system platforms on disks capable of being driven in a manner similar to CDs or DVDs. Generally speaking, in such systems, the disk, which comprises of a plurality of assays, each having a number of chambers and microchannels containing the components necessary for conducting the given test/analysis, is rotated at predetermined speeds. As a result of the centrifugal force generated by the rotation of the disk, the chemicals, fluids, samples, etc. move through the chambers/microchannels of the given assay, and a result is generated.

U.S. Pat. No. 6,063,589, which is herein incorporated by reference, illustrates an example of a micro-system platform formed on a CD type disk. For example, referring to FIGS. 1 and 2 thereof, the assay array 12 includes a sample entry port 201 which is connected with an array of metering capillaries 202. The entry port is coupled to an overflow capillary 203, which is connected to an overflow chamber 205. The metering capillaries are also coupled to a fluid chamber 204. Each of the overflow and fluid chamber is coupled with an air channel, for example, channel 211. The assay further includes a holding chamber 207 which is connected to the fluid chamber 204 via capillary 206. Finally, the assay includes a read chamber 210 coupled to the holding chamber 207 as valve 213.

As explained in detail in the '589 patent, by various means, e.g., centrifugal force, a portion of a sample input via the sample entry port is moved through the various capillaries, and possibly mixed with reagents already disposed with the chambers, in accordance with the given assay being conducted, so as to perform the desired test/analysis associated with the given assay. In one example, the result of the assay is determined based on the presence or absence of an analyte, which if present will be contained in the read chamber 210.

U.S. Pat. No. 6,030,581, which is also incorporated herein by reference, illustrates another example of a micro-system platform formed utilizing a disk type format. Referring to FIG. 1 thereof, the micro-system platform contains two sectors: an assay sector 11 and a software sector 12. The assay sector 11, which operates on a given sample, can be formed of one of more of the components illustrated in FIG. 2A. Examples of particular assays are set forth in FIGS. 2B and 4. The software sector 12 contains instructions for controlling the rotation regimen of the disk associated with the given assay contained in the assay sector 11.

Notwithstanding the foregoing known micro-system platforms formed utilizing disk formats, problems remain. For example, known micro-system platforms do not provide for the recordation of the results of the analysis as the analysis pertains to a particular patient, or for recordation of a test log. In addition, the design of known micro-platforms inherently limit the amount of disk space available for storing control commands and the amount of disk space available for assays. Further, known micro-system platforms do not provide for retrieval of control information in an optimum manner, thereby causing a decrease in the overall operating speed of the micro-system platform.

Accordingly, there remains a need for providing a micro-system platform capable of storing data associated with patient results and records, as well as a test log associated with performance of the actual test. In addition, there is a need for a micro-system platform which optimizes the space available for data storage and assays, and which optimizes the reading and writing of such data so as to maximize the overall operating speed of the system.

It is the object of the present invention to correct the foregoing deficiencies in the prior art.

SUMMARY OF THE INVENTION

In general, the present invention relates to a micro-system platform that provides for the recordation of patient information, test results associated with individual patients, test log information and control information associated with the particular assay to be conducted. In addition, the design of the micro-platform of the present invention is such that it optimizes both the amount of data that can be recorded/stored and the number of assays to be accommodated on a single disk, as well as the time associated with reading and writing information/data.

In a first exemplary embodiment, the present invention relates to an apparatus for performing an assay, where the apparatus comprises a micro-system platform, a CD-ROM device and an information processor. The CD-ROM device is under control of the information processor and is capable of reading and writing data to the micro-system platform. The micro-system platform comprises a first section for storing data in a continuous circular data band, which is disposed in an inner portion of the micro-system platform, and a second section including at least one assay, which is formed in an outer portion of the micro-system platform. During operation, the CD-ROM device retrieves and stores data relating to the performance of the assay in the data band. The information processor is operative for controlling the CD-ROM device in accordance with the data retrieved from the data band so as to conduct the assay, and for analyzing the results of the assay.

The present invention also relates to a method of conducting an assay utilizing an apparatus comprising a micro-system platform, a CD-ROM device and an information processor, where the micro-system platform comprises a first section for storing data in a continuous circular data band disposed in an inner portion of the micro-system platform, and a second section including at least one assay formed in an outer portion of said micro-system platform. The method comprises the steps of retrieving data related to the performance of the assay from the circular data band, controlling the CR-ROM device in accordance with the data retrieved from the circular data band so as to manipulate the micro-system platform as required to conduct the assay, analyzing the results of the assay, and storing data indicative of the results of the assay in the circular data band.

As described in further detail below, the present invention provides significant advantages over the prior art. Most importantly, the micro-system platform of the present invention is capable of storing data associated with patient results and records, as well as a test log associated with performance of the actual assay on the given micro-system platform. As a result, all information pertaining to the performance and results of a given test is stored within a single medium (i.e., the micro-system platform), and these results can be re-examined in future years without any degradation or loss of relevant information. Thus, the present invention improves the integrity of maintaining such test results over an extended period of time as all pertinent information is contained on the micro-system platform.

Another advantage provided by the micro-system platform of the present invention is that it optimizes the space available for data storage and assays for a given platform size, as well as optimizes the reading and writing of data to the micro-system platform so as to maximize the overall operating speed of the system. In particular, as explained below, by forming the information/data band as a single continuous track, the retrieval/access time associated with retrieving or storing data is minimized, thereby allowing for faster overall operation.

An additional advantage of the present invention is that it allows the CDROM software to automatically start reading from the inner most track, and continue reading in a contiguous manner, thereby allowing the present invention to take advantage of all the existing technology for CD type drives.

Additional advantages of the present invention will become apparent to those skilled in the art from the following detailed description of exemplary embodiments of the present invention.

The invention itself, together with further objects and advantages, can be better understood by reference to the following detailed description and the accompanying drawings.

DETAILED DESCRIPTION OF THE DRAWINGS

Figure 1:
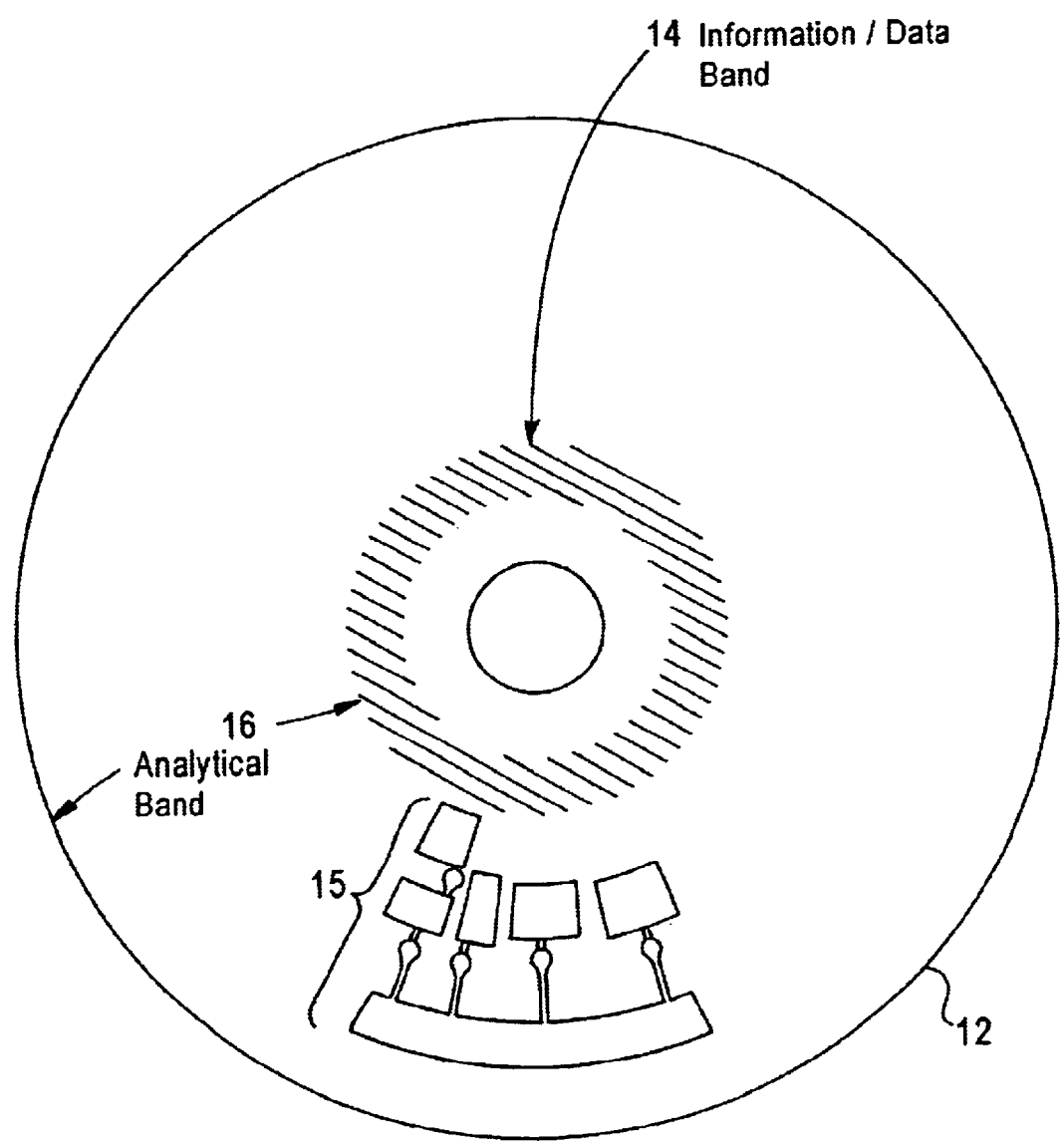
FIG. 1 illustrates an exemplary embodiment of the micro-system platform utilizing a disk structure in accordance with the present invention.

FIG. 1 illustrates an exemplary embodiment of the micro-system platform 10 of the present invention. Referring to FIG. 1, the micro-system platform 10 comprises a disk 12 which is divided into two bands, namely an information/data band 14 and an analytical band 16. As explained in more detail below, preferably, the information/data band 14 is a continuous band beginning at the inner diameter of the disk 12. The band 14 forms a continuous circular unbroken track, which continually expands the overall width of the band 14, as the track is made longer. In the preferred embodiment, the band is formed utilizing standard compact disk (CD) technology. It is noted that the overall length of the track (i.e., width of the band 14) can be varied in accordance with the amount of storage capacity necessary for the given micro-system platform and assays contained therein. It is further noted that the overall diameter of the disk 12 can be varied In accordance the given micro-system platform and assays contained therein, as well as the device (i.e. CD drive) utilized to spin the disk 12. In other words, the present invention is compatible with any size disk.

The analytical band 16 contains the given assay to be performed. It is noted that it is possible for the analytical band 16 to contain a plurality of assays, each of which is disposed in a given section in the outside portion of the disk 12. It is further noted that in the embodiment illustrated in FIG. 1, the analytical band 16 does not extend into or overlap with the information/data band 14. However, it is also possible that the information/data band be disposed on one side (e.g., top side) of the disk and the assays be disposed on the opposite side (e.g., bottom side) of the disk. When arranged in such a manner, it is possible for the information/data band and the analytical band to overlap. The information/data band and the analytical band cannot share the same space on the same layer. Element 15 of FIG. 1 illustrates an exemplary assay.

The actual assay(s) contained in the analytical band 16 can be any known assay capable of being implemented on a disk. Typically, an assay contains one or more of the following components: capillaries, containers, filters, dialysis membranes, chromatographic columns, electrophoretic gels, valves, any micromechanical or electronic components including microprocessors, electrodes, cuvettes and assay elements. Possible operations performed by the foregoing components include centrifugation, filtering, transfer of liquids, mixing of liquids, dialysis, column separations, heating, cooling, electroconvection, electrophoresis and analyte detection and signaling thereof.

The disk 12 is typically made from two planar surfaces forming upper and lower halves, although it is noted that the disk may contain additional layers. In one embodiment, the planar surface forming the lower surfaces contains substantially all of the components utilized to form the desired assay, as well as the grooves and chemicals associated with the formation of the information/data band 14 necessary for providing for the reading, writing and erasing of data contained therein.

Figure 3:
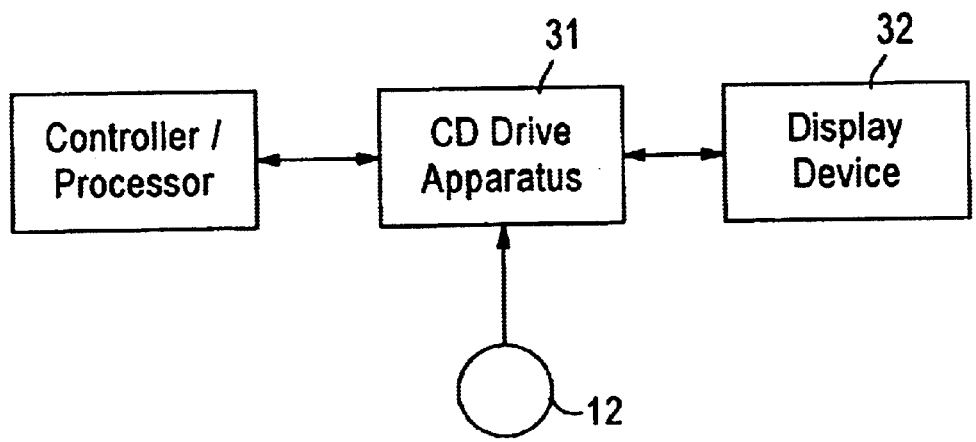
FIG. 3 is a block diagram illustrating an exemplary system for processing the micro-system platform of the present invention.

Referring again to FIG. 1, as indicated above, the information/data band 14 provides for the storage and recording of data associated with the given assay to be performed. For example, the information stored in the band 14 may relate to operating instructions necessary to perform the test associated with the give assay (e.g., when and how to insert a sample into an entry port of an assay). Of course, the data band 14 can also contain any other instruction or operation necessary to be performed in accordance with the assay of the given micro-system platform. Referring to FIG. 3, which illustrates an exemplary system 30 utilized in conjunction with the micro-system platform 10, such instructions are read by a CD drive apparatus 31 capable of reading data encoded on the disk 12 and then, if appropriate, displayed to the operator utilizing a display screen 32. Alternatively, if the instructions can be performed automatically, the CD drive apparatus 31 does so. It is noted that the CD drive apparatus 31 is typically under control of a microcontroller 33 (e.g., computer), and is typically a standard CD drive, which is modified to provide for the steps required by the assay (e.g., variations in rotational speed, heating of disk, etc.). The microcontroller 33 functions to interpret the information/data received from the disk 12 and control the CD drive apparatus 31 in accordance with such information. Of course, it is possible to include the microcontroller 33 within the CD drive apparatus 31.

Preferably, the information/data band 14 also contains commands to be executed in conjunction with the given assay. For example, such commands include the specific rotational control requirements, such as, acceleration, speed, deceleration, vibration, and the time period associated with each specific requirement. Other examples of such commands, include the heating and/or cooling of the disk and the associated time period thereof. In operation, this control information is read from the information/data band 14 and then the CD drive apparatus 31 is automatically controlled in accordance with the instruction so as to perform the required process.

In accordance with the preferred embodiment of the present invention, information/data is also capable of being written (i.e., stored) to the information/data band 14 during execution of the given assay. The disk 12 may be enabled in either a write once mode, or in a read/erase/rewrite mode. In the preferred embodiment, a log of the actual mechanical activity of the disk 12 during performance of the assay is maintained (e.g., disk spun at 300 rpm for 35 secs, then heated at temperature X for 2 minutes, etc.). In other words, a test log recording every aspect of how the disk 12 was actually manipulated during the performance of the assay is recorded. Importantly, this test log represents that actual mechanical movement and physical treatment of the disk 12 during the test process. Such information can prove useful for determining whether or not the assay was performed accurately, and more importantly, provides a permanent record of the assay performed and the assay results on a single disk. The results of the assay are also stored in the band 14. In order to provide for the generation of the foregoing test log, the CD drive apparatus 31 is provided with sensors to allow for the necessary measurements of such mechanical/physical data (e.g., actual rotation speed, time duration of rotation, temperature, etc.).

Continuing, in the preferred embodiment, the information/data band 14 also includes information identifying the origin of the assay sample, such as patient names, patient statistics, patient history or patient identification codes. More specifically, the patient information, assay results associated with the given patient and the aforementioned assay test log (indicating the actual activity performed) are all stored in the information data band 14. By providing for the storage of all of the foregoing information in the information/data band 14, the present invention eliminates the integrity problems that arise if such information is maintained separately (i.e., on different mediums or in different locations). Indeed, by reading the information stored in band 14, it will immediately be determined the type of assay executed, the results of the assay and the corresponding patient information. This remains true even years after the testing has been conducted. It is noted that it is possible to store information regarding multiple patients and assay results on a single disk. Moreover, it is further noted that it is also possible to store any other desired information associated with the given assay in the band 14.

Moreover, as a result of utilizing the "band" format to store the relevant information and data, the present invention operates with increased speed in comparison to known prior art devices. In particular, because of the use of the information/data band 14, all of the relevant, necessary information is contained in a single continuous track. As such, the retrieval/access time associated with retrieving or storing data is minimized. For example, assuming data storage was divided into sectors as opposed to the "band" of the present invention, then during the reading or writing of data in such a sectored disk, it will often be necessary for the CD drive to suspend reading/writing of data as the desired sector is continuously rotated during operation. This results in an increase in the time required for the reading/writing of data. In addition, it is also likely that the CD drive would enter some kind of error recovery route upon encountering a sector that was not an information band, thereby further increasing the time required for reading/writing to the disk.

In contrast, the band format of the present invention allows all relevant data, for example, for a given patient (which may be, but is not limited to, a human, an animal, a plant or almost any kind of source material), to be stored continuously within the information/data band 14, thereby eliminating the need for continuously starting and stopping the reading/writing process as required when utilizing a sector format. In addition, the "band" format also provides for maximization of the amount of data that can be stored on a single disk, by eliminating "dead space" that, for example, may be associated with disks segregated by sectors, where each sector is designated a predetermined amount of data storage capability. As stated above, additional storage space can be added to the information/data band by simply increasing the width of the band.

In one embodiment of the present invention, the information/data band 14 comprises a unique identification code, which identifies the disk as a bioanalytical disk rather than a multimedia or data only CD disk. In the preferred embodiment, the unique identification code is the first information stored in the band 14 such that it is the first data read by the CD drive. The identification code functions to notify the CD drive that the disk is a bioanalytical disk. Upon receiving such information, assuming the CD drive is capable of multiple modes of operation, the CD drive enables the command set associated with such bioanalytical analysis. Of course, the unique identification code can be substantially any predefined code that the CD drive is programmed to recognize as identifying a bioanalytical disk.

Figure 2:
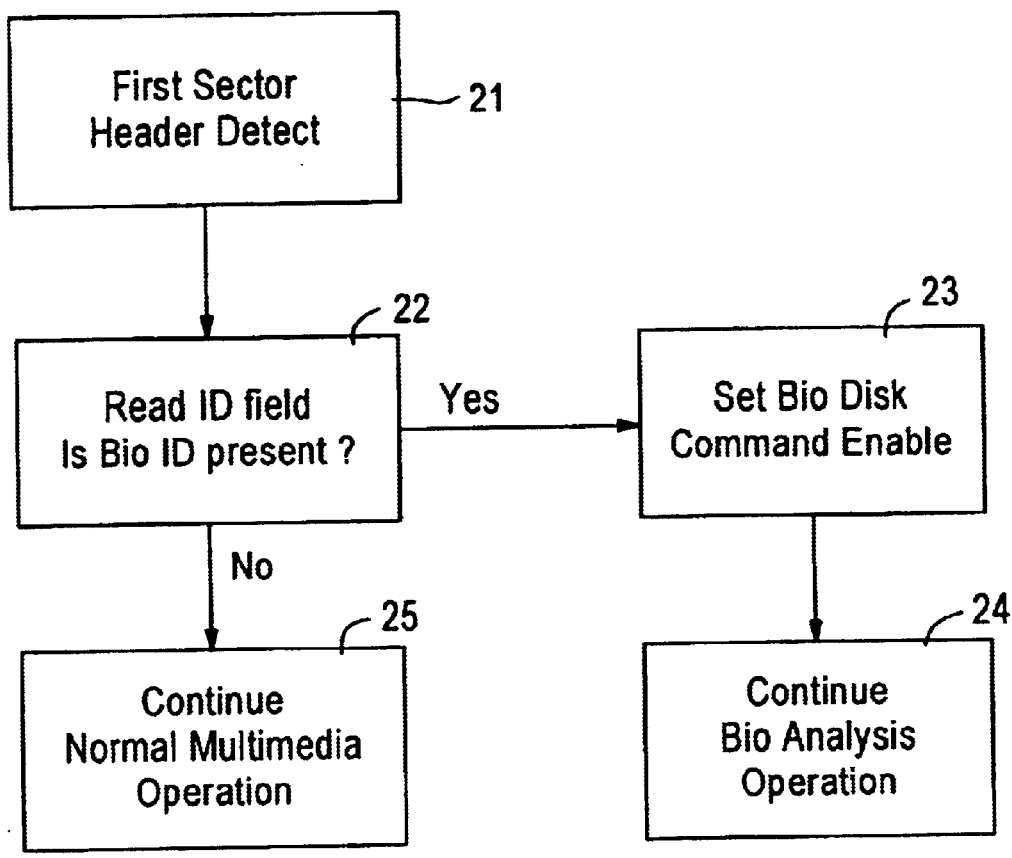
FIG. 2 is a flow chart illustrating the operation of the exemplary embodiment of the present invention illustrated in FIG. 1.

FIG. 2 is a flow chart illustrating the operation of such a CD drive capable of receiving and operating the bioanalytical disk, including identification of the unique identification code. In the first step 21, the CD drive reads the first section of the information/data band 14 to determine whether the unique identification code is present (step 22). If the code is present, the CD drive enables the mode of operation associated with such bioanalytical analysis (step 23), and the CD drive proceeds with the bioanalysis operation in accordance with the instructions read from the information/data band 14 (step 24). If the code is not present, the CD drive proceeds with normal operation utilized for processing a multimedia disk (step 25).

As described above, the present invention provides significant advantages over the prior art. Most importantly, the micro-system platform of the present invention is capable of storing data associated with patient results and records, as well as a test log associated with performance of the actual assay on the given micro-system platform. As a result, all information pertaining to the performance and results of a given test is stored within a single medium (i.e., the micro-system platform), and these results can be re-examined in future years without any degradation or loss of relevant information. Thus, the present invention improves the integrity of maintaining such test results over an extended period of time as all pertinent information is contained on the micro-system platform.

Another advantage provided by the micro-system platform of the present invention is that it optimizes the space available for data storage and assays for a given platform size, as well as optimizes the reading and writing of data to the micro-system platform so as to increase the overall operating speed of the system. In particular, by forming the information/data band as a single continuous track, the retrieval/access time associated with retrieving or storing data is minimized, thereby allowing for faster overall operation.

It is also noted that variations of the exemplary embodiments disclosed above are also possible. For example, it is possible to form the disk such that data may only be written once into the data band, and once written, cannot be erased.

In addition, as already stated above, it is possible to vary the width of the data band in accordance with the amount of data to be stored therein in association with the assays of the micro-system platform.

In addition, it is also possible to provide data on the disk which informs the CD drive apparatus the precise location of the results of each assay contained on the disk, as well as commands regarding how to read the assay results. For example, various assays may be read utilizing optical detection components. Such commands contained on the disk may instruction the CD drive of the brightness level of a "read" signal necessary to properly determine the test result. Alternatively, the command may provide for intensity adjustments for reading/identifying different analytes. In another variation, the commands contained on the disk may provide for adjusting the sensitivity of an optical sensor to enhance the detection of a specific analyte.

Although certain specific embodiments of the present invention have been disclosed, it is noted that the present invention may be embodied in other forms without departing from the spirit or essential characteristics thereof. The present embodiments are therefor to be considered in all respects as illustrative and not restrictive, the scope of the invention being indicated by the appended claims, and all changes that come within the meaning and range of equivalency of the claims are therefore intended to be embraced therein.

I claim:

1. A micro-system platform capable of being read by a disk device, said micro-system platform comprising:
    a first section for storing data in a continuous circular data band, said data band being disposed in an inner portion of said micro-system platform, and
    a second section including at least one assay, said second section forming an outer portion of said micro-system platform.

2. The micro-system platform of claim 1, wherein said platform comprises a rotatable, circular substrate, said substrate having a first flat planar surface and a second flat planar surface, wherein said one of said first flat planar surface and said second flat planar surface comprises components forming said assay, and said other of said first flat planar surface and said second flat planar surface comprises said data band.

3. The micro-system platform of claim 1, wherein said data band comprises a continuous groove which begins at an inner portion of said first section, and which expands in a spiral, circular manner.

4. The micro-system platform of claim 3, wherein said data band comprises a unique data code identifying said micro-system platform as a bioanalytical disk.

5. The micro-system platform of claim 3, wherein said data band comprises data regarding the procedures necessary for conducting said assay.

6. The micro-system platform of claim 3, wherein said data band comprises data regarding the actual mechanical activity of said platform during the time period said assay is being performed and the results of performing said assay.

7. The micro-system platform of claim 3, wherein said data band comprises data regarding patient information, said patient information including information selected from the group consisting of patient name, patient address, patient age, results of said assay associated with a given patient and patient statistics.

8. The micro-system platform of claim 3, wherein said second section of said micro-system platform comprises a plurality of assays.

9. The micro-system platform of claim 8, wherein at least two of said plurality of assays perform different functions.

10. The micro-system platform of claim 3, wherein data can be written into said data band, read from said data band and erased from said data band.

11. An apparatus for performing an assay, said apparatus comprising a micro-system platform, a disk device and an information processor,
    said micro-system platform capable of being read by a disk device, said micro-system platform comprising:
    a first section for storing data in a continuous circular data band, said data band being disposed in an inner portion of said micro-system platform, and
    a second section including at least one assay, said second section forming an outer portion of said micro-system platform,
    wherein said disk device is operative for retrieving and storing data in said circular data band, said data being related to the performance of said assay, and said information processor is operative for controlling said disk device in accordance with the data retrieved from said circular data band, and for analyzing the results of said assay.

12. The apparatus of claim 11, wherein said platform comprises a rotatable, circular substrate, said substrate having a first flat planar surface and a second flat planar surface, wherein said one of said first flat planar surface and said second flat planar surface comprises components forming said assay, and said other of said first flat planar surface and said second flat planar surface comprises said data band.

13. The apparatus of claim 11, wherein said data band comprises a continuous groove which begins at an inner portion of said first section, and which expands in a spiral, circular manner.

14. The apparatus of claim 13, wherein said data band comprises a unique data code identifying said micro-system platform as a bioanalytical disk.

15. The apparatus of claim 13, wherein said data band comprises data regarding the procedures necessary for conducting said assay, said information processor controlling said disk device to perform said procedures.

16. The apparatus of claim 13, wherein said data band comprises data regarding the actual mechanical activity of said platform during the time period said assay is being performed and the results of performing said assay.

17. The apparatus of claim 13, wherein said data band comprises data regarding patient information, said patient information including information selected from the group consisting of patient name, patient address, patient age, results of said assay associated with a given patient and patient statistics.

18. The apparatus of claim 13, wherein said second section of said micro-system platform comprises a plurality of assays.

19. The apparatus of claim 18, wherein at least two of said plurality of assays perform different functions.

20. The apparatus of claim 13, wherein said disk device can write data into said data band, read data from said data band and erase data from said data band.

21. A method for performing an assay utilizing an apparatus comprising a micro-system platform, a disk device and an information processor, wherein said micro-system platform comprises a first section for storing data in a continuous circular data band, said data band being disposed in an inner portion of said micro-system platform, and a second section including at least one assay, said second section forming an outer portion of said micro-system platform, said method comprising the steps of:

retrieving data from said circular data band, said data being related to the performance of said assay, controlling said disk device in accordance with the data retrieved from said circular data band so as to manipulate said micro-system platform as required to conduct said assay, analyzing the results of said assay, and storing data indicative of the results of said assay in said circular data band.

22. The method of claim 21, wherein said platform comprises a rotatable, circular substrate, said substrate having a first flat planar surface and a second flat planar surface, wherein said one of said first flat planar surface and said second flat planar surface comprises components forming said assay, and said other of said first flat planar surface and said second flat planar surface comprises said data band.

23. The method of claim 21, wherein said circular data band comprises a continuous groove which begins at an inner portion of said first section, and which expands in a spiral, circular manner.

24. The method of claim 23, further comprising the step of storing data representing a unique code in said circular data band, said unique code identifying said micro-system platform as a bioanalytical disk.

25. The method of claim 23, further comprising the step of storing data regarding the actual mechanical activity of said platform during the time period said assay is being performed.

26. The method of claim 23, further comprising the step of storing data in the circular data band related to patient information, said patient information including information selected from the group consisting of patient name, patient address, patient age, results of said assay associated with a given patient and patient statistics.

27. The method of claim 23, wherein said second section of said micro-system platform comprises a plurality of assays.

28. The method of claim 27, wherein at least two of said plurality of assays perform different functions.

29. The method of claim 23, wherein said disk device can write data into said circular data band, read data from said circular data band and erase data from said circular data band.

30. The micro-system platform of claim 1 wherein said disk device is a CD-ROM device.

31. The micro-system platform of claim 1, wherein the data band includes a portion at the inner most track of the platform so that said disk device can automatically start reading from the inner most track.

32. The apparatus of claim 11, wherein said disk device is a CD-ROM device.

33. The apparatus of claim 11, wherein the data band includes a portion at the inner most track of the platform so that said disk device can automatically start reading from the inner most track.

34. The method of claim 21, wherein said disk device is a CD-ROM device.

35. The method of claim 21, wherein the data band includes a portion at the inner most track of the platform, said method further comprising the step of automatically starting reading from the inner most track.

* * * * *